(12) United States Patent
Cheung et al.

(10) Patent No.: US 10,010,689 B2
(45) Date of Patent: Jul. 3, 2018

(54) NASAL CANNULA SYSTEM AND METHOD

(71) Applicant: KONINKLIJKE PHILIPS N.V., Eindhoven (NL)

(72) Inventors: Waiman Cheung, Tarentum, PA (US); Jeffrey Coles, Irwin, PA (US); Norbert Hans Balko, Harrison City, PA (US); Edmund Arnliot Shaw, Monroeville, PA (US)

(73) Assignee: Koninklijke Philips N.V., Eindhoven (NL)

(*) Notice: Subject to any disclaimer, the term of this patent is extended or adjusted under 35 U.S.C. 154(b) by 450 days.

(21) Appl. No.: 14/442,406

(22) PCT Filed: Dec. 4, 2013

(86) PCT No.: PCT/IB2013/060613
§ 371 (c)(1),
(2) Date: May 13, 2015

(87) PCT Pub. No.: WO2014/091362
PCT Pub. Date: Jun. 19, 2014

(65) Prior Publication Data
US 2016/0271353 A1    Sep. 22, 2016

Related U.S. Application Data

(60) Provisional application No. 61/735,585, filed on Dec. 11, 2012.

(51) Int. Cl.
*A61M 16/06* (2006.01)
*A61M 16/00* (2006.01)
*A61M 16/12* (2006.01)

(52) U.S. Cl.
CPC .... *A61M 16/0672* (2014.02); *A61M 16/0666* (2013.01); *A61M 16/0627* (2014.02); *A61M 16/122* (2014.02); *A61M 2016/0027* (2013.01)

(58) Field of Classification Search
CPC .......... A61M 16/0666; A61M 16/0672; A61M 16/0677; A61M 16/0808; A61M 16/1045;
(Continued)

(56) References Cited

U.S. PATENT DOCUMENTS 6,158,430 A     12/2000  Pfeiffer et al.
6,595,215 B2 *  7/2003   Wood ................ A61M 16/0666
                                                    128/207.13
(Continued)

FOREIGN PATENT DOCUMENTS

DE    102007026565 A1    12/2007
FR    2827778 A1         1/2003

*Primary Examiner* — Steven Douglas

(57) ABSTRACT

Described herein is a nasal cannula apparatus. The apparatus is configured to detect the pressurized flow of breathable gas to and/or from the airway of a subject through the nose of the subject. The apparatus comprises a body, a first nasal cannula system formed in the body configured to engage a first nostril of a first nasal passage, and a second nasal cannula system formed in the body configured to engage a second nostril of a second nasal passage of the subject. The second nasal cannula system is joined to first nasal cannula system by a bridge such that the first nasal cannula system engages the first nostril and second nasal cannula system engages the second nostril at the same time. The apparatus is configured to transmit expiratory and inspiratory nasal pressurized flow to connective conduits.

20 Claims, 6 Drawing Sheets

(58) Field of Classification Search
CPC .................. A61M 16/16; A61M 15/08; A61M 2016/0027; A61M 16/0627; A61M 16/122; A62B 23/06; A62B 9/003; A62B 9/06

See application file for complete search history.

(56) References Cited

U.S. PATENT DOCUMENTS

| | | | |
|---|---|---|---|
| 6,679,265 B2* | 1/2004 | Strickland | A61M 16/0666 128/207.13 |
| 7,234,465 B2* | 6/2007 | Wood | A61M 16/0666 128/206.11 |
| 8,156,937 B2 | 4/2012 | De Vries et al. | |
| 8,839,791 B2* | 9/2014 | Allum | A61M 16/0666 128/201.13 |
| 8,939,152 B2* | 1/2015 | Wondka | A61M 11/005 128/206.18 |
| 9,327,092 B2* | 5/2016 | Brambilla | A61M 16/0875 |
| 2003/0079749 A1 | 5/2003 | Strickland et al. | |
| 2005/0028821 A1 | 2/2005 | Wood et al. | |
| 2006/0107958 A1 | 5/2006 | Sleeper | |
| 2006/0174887 A1 | 8/2006 | Chandran et al. | |
| 2007/0113856 A1 | 5/2007 | Acker | |
| 2007/0299358 A1 | 12/2007 | Bertinetti et al. | |
| 2009/0069646 A1 | 3/2009 | Yamamori et al. | |
| 2009/0133699 A1* | 5/2009 | Nalagatla | A61B 5/0836 128/205.27 |
| 2011/0094518 A1 | 4/2011 | Cipollone et al. | |
| 2012/0080033 A1 | 4/2012 | Varga | |

* cited by examiner

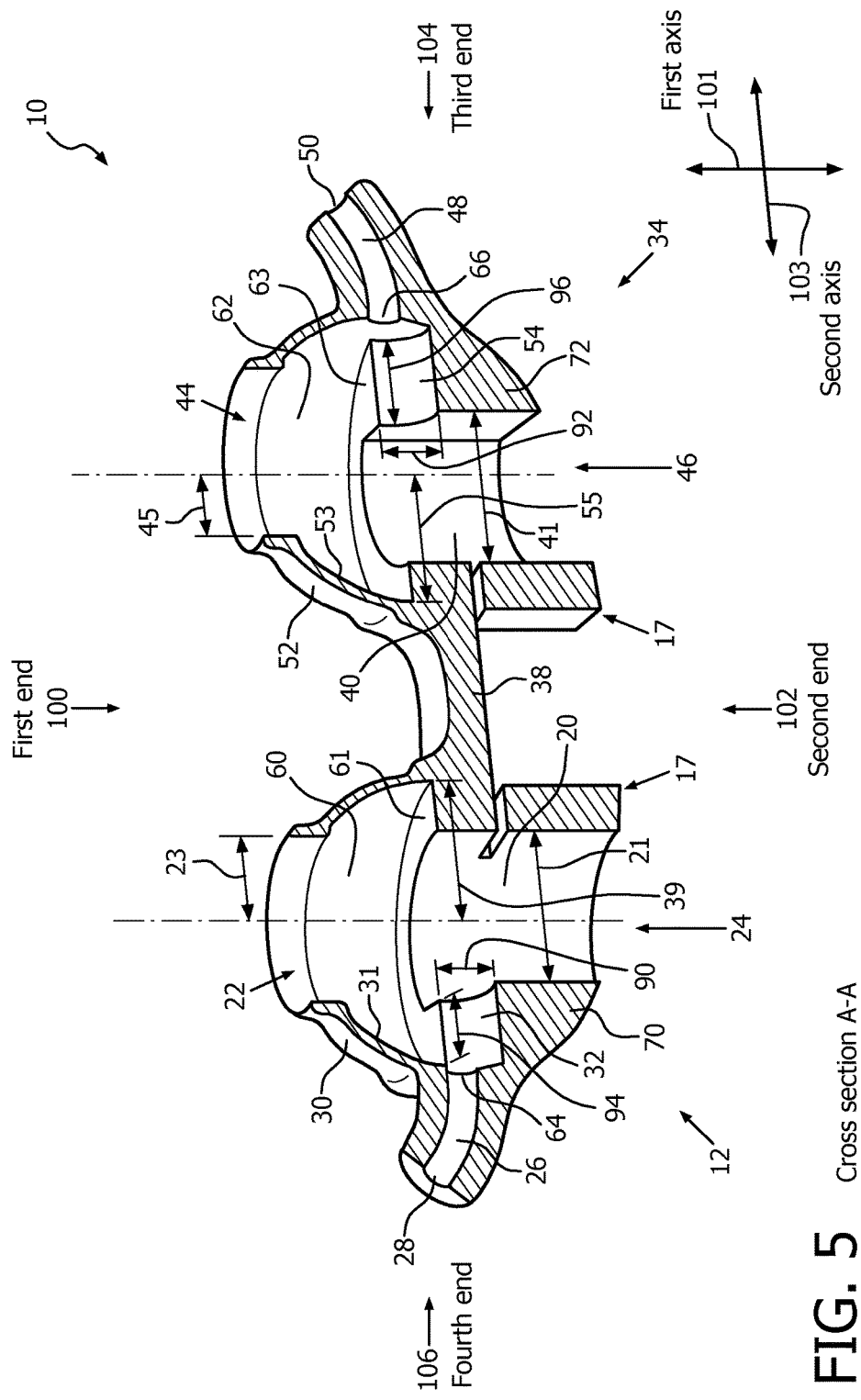
FIG. 5  Cross section A-A

US 10,010,689 B2

NASAL CANNULA SYSTEM AND METHOD

CROSS-REFERENCE TO PRIOR APPLICATIONS

This application is the U.S. National Phase application under 35 U.S.C. § 371 of International Application Serial No. PCT/IB2013/060613, filed on Dec. 4, 2013, which claims the benefit of U.S. Application Ser. No. 61/735,585, filed on Dec. 11, 2012. These applications are hereby incorporated by reference herein.

BACKGROUND

1. Field

The present disclosure pertains to a nasal cannula apparatus.

2. Description of the Related Art

Nasal cannulas are known. A cannula is often worn during monitoring of a patient's inspiratory and expiratory nasal pressure such as during a sleep study. A conventional nasal cannula requires the insertion of prongs into the patient's nasal passage. Conventional nasal cannula prongs are comparatively smaller (in diameter) than a patient's nasal passage. Conventional nasal cannula prongs may generate irritation and discomfort when the prongs move within the patient's nasal passage. Discomfort and irritation generated by conventional nasal cannula prongs may wake a sleeping patient and interrupt a sleep study. Often, conventional nasal cannulas require the utilization of higher durometer elastomeric materials to ensure nasal prong shape retention during patient use. Higher durometer materials are stiff, resulting in a higher degree of irritation and discomfort when placed within a patient's nasal passage.

SUMMARY

Accordingly, one or more aspects of the present disclosure relate to a nasal apparatus comprising a first nasal cannula system configured to engage a nose of a subject. The nose includes a first nostril, a second nostril, a first nasal passage, and a second nasal passage. The first nasal cannula system comprises a first breathing conduit, a first pressure conduit, a first sealing surface, and a first flow deflection surface. The first breathing conduit is configured to conduct a pressurized flow of breathable gas into one or both nasal passages of the subject through a first nasal port during inhalation, and conduct exhaled gas out of one or both nasal passages to the ambient environment through a first ambient environment port during exhalation. The first nasal port is open to one or both nasal passages of the subject. The first ambient environment port is open to the ambient environment. The first sealing surface surrounds the first nasal port and is configured to removably seal the first nasal cannula system with one or both nostrils to prevent gas from escaping between the first sealing surface and one or both nostrils. During inspiration, breathable gas flows through the first breathing conduit, drawing breathable gas from the first pressure conduit to the first breathing conduit, creating negative pressurized flow in the first pressure conduit, to the first pressure port. The portion of inhaled gas creates negative pressurized flow at the first pressure port such that one or more gas parameters of the gas in the first pressure conduit are impacted sufficiently to facilitate quantification of such one or more gas parameters in one or both nasal passages of the subject from measurements taken on the pressurized flow of breathable gas upstream of delivery from the first breathing conduit into one or both nasal passages of the subject. During expiration, breathable gas flows out of one or both nasal passages, through the first breathing conduit, to the ambient environment through the first ambient environment port. At least a portion of the breathable gas is deflected by the first flow deflection surface toward the first pressure conduit, creating positive pressurized flow in the first pressure conduit, to the first pressure port. The portion of exhaled gas is deflected such that one or more gas parameters of the gas in the first pressure conduit are impacted sufficiently to facilitate quantification of such one or more gas parameters in one or both nasal passages of the subject from measurements taken on the pressurized flow of breathable gas upstream of delivery from the first breathing conduit into one or both nasal passages of the subject.

Yet another aspect of the present disclosure relates to a method for engaging a nose of a subject with a nasal apparatus. The apparatus comprises a first nasal cannula system. The first nasal cannula system comprises a first breathing conduit, a first pressure conduit, a first sealing surface, and a first flow deflection surface. The nose includes a first nostril, a second nostril, a first nasal passage, and a second nasal passage. The method comprises: conducting, with the first breathing conduit, a pressurized flow of breathable gas into one or both nasal passages of the subject through a first nasal port during inhalation, and conducting exhaled gas out of one or both nasal passages to the ambient environment through a first ambient environment port during exhalation, the first nasal port open to one or both nasal passages of the subject, the first ambient environment port open to the ambient environment; conducting, with the first pressure conduit, the pressurized flow of breathable gas from a first pressure port to the first breathing conduit during inhalation, the first pressure port configured to receive the pressurized flow of breathable gas during inhalation; surrounding, with the first sealing surface, the first nasal port, and removably sealing, with the first sealing surface, the first nasal cannula system with one or both nostrils to prevent gas from escaping between the first sealing surface and one or both nostrils; and deflecting, with the first flow deflection surface, at least a portion of the exhaled gas from the first breathing conduit into the first pressure conduit during exhalation such that one or more gas parameters of the gas in the first pressure conduit are impacted sufficiently to facilitate quantification of such one or more gas parameters in one or both nasal passages of the subject from measurements taken on the pressurized flow of breathable gas upstream of delivery from the first breathing conduit into one or both nasal passages of the subject.

Still another aspect of the present disclosure relates to a nasal apparatus comprising a first means for engaging a nose of a subject. The nose includes a first nostril, a second nostril, a first nasal passage, and a second nasal passage. The first means for engaging comprising: a first means for conducting a pressurized flow of breathable gas into one or both nasal passages of the subject through a first nasal port during inhalation, and conducting exhaled gas out of one or both nasal passages to the ambient environment through a first ambient environment port during exhalation, the first nasal port open to one or both nasal passages of the subject, the first ambient environment port open to the ambient environment; a first means for conducting the pressurized flow of breathable gas from a first pressure port to the first means for conducting the pressurized flow of breathable gas into one or both nasal passages through the first nasal port during inhalation, the first pressure port configured to receive the pressurized flow of breathable gas during inhalation; a first means for surrounding the first nasal port and removably sealing the first means for engaging the nose of the subject with one or both nostrils to prevent gas from escaping between the first means for surrounding and sealing and one or both nostrils; and a first means for deflecting at least a portion of the exhaled gas from the first means for conducting the pressurized flow of breathable gas into one or both nasal passages of the subject into the first means for conducting the pressurized flow of breathable gas from the first pressure port during exhalation such that one or more gas parameters of the gas in the first means for conducting the pressurized flow of breathable gas from the first pressure port are impacted sufficiently to facilitate quantification of such one or more gas parameters in one or both nasal passages of the subject from measurements taken on the pressurized flow of breathable gas upstream of delivery from the first means for conducting the pressurized flow of breathable gas into one or both nasal passages of the subject.

These and other objects, features, and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the disclosure.

BRIEF DESCRIPTION OF THE DRAWINGS

FIG. 5 illustrates a cross-sectional view of the minimally invasive nasal apparatus.

DETAILED DESCRIPTION OF EXEMPLARY EMBODIMENTS

Figure 1:
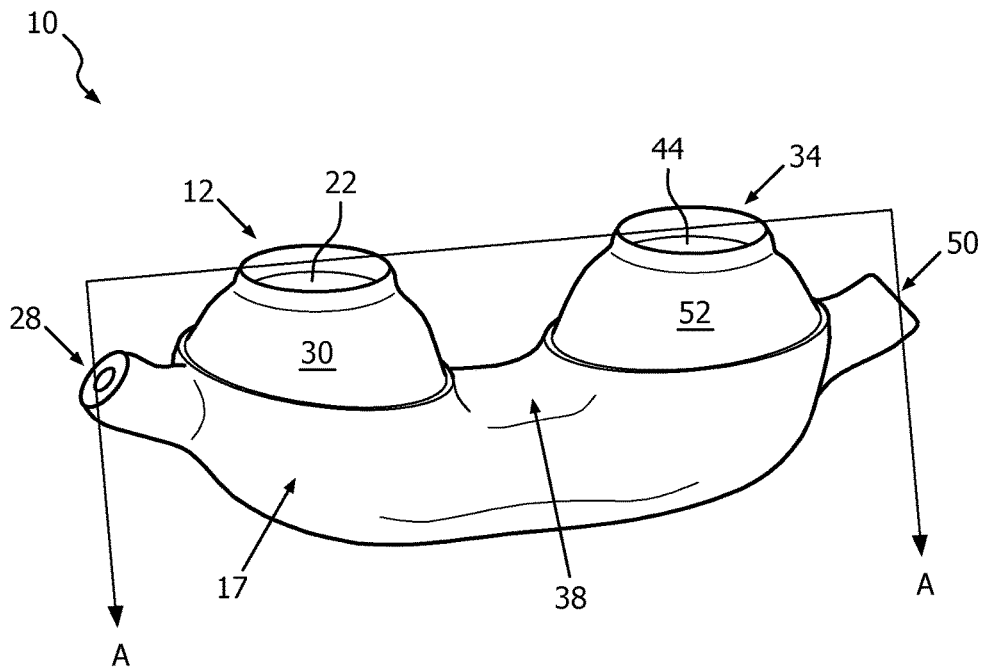
FIG. 1 is an illustration of a minimally invasive nasal apparatus.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

FIG. 1 is an illustration of a nasal apparatus 10. Apparatus 10 is configured to detect a flow of gas to and/or from the airway of a subject through the nose of the subject. In some embodiments, apparatus 10 is minimally invasive. As such, apparatus 10 removably engages an area (or areas) surrounding one or both nostrils of the nose of the subject to communicate gas to and/or from the airway of the subject. In some embodiments, minimally invasive nasal apparatus 10 comprises a body 17, a first nasal cannula system 12 formed in body 17 configured to engage a first nostril of a first nasal passage and a second nasal cannula system 34 formed in body 17 configured to engage a second nostril of a second nasal passage of the subject. Second nasal cannula system 34 is joined to first nasal cannula system 12 by a bridge 38 such that first nasal cannula system 12 engages the first nostril and second nasal cannula system 34 engages the second nostril at the same time. In some embodiments, apparatus 10 is configured to transmit expiratory and inspiratory nasal pressure to connective conduits as a closed system. This closed system has been moved externally through the introduction of an open system from an air-flow perspective.

Figure 2:
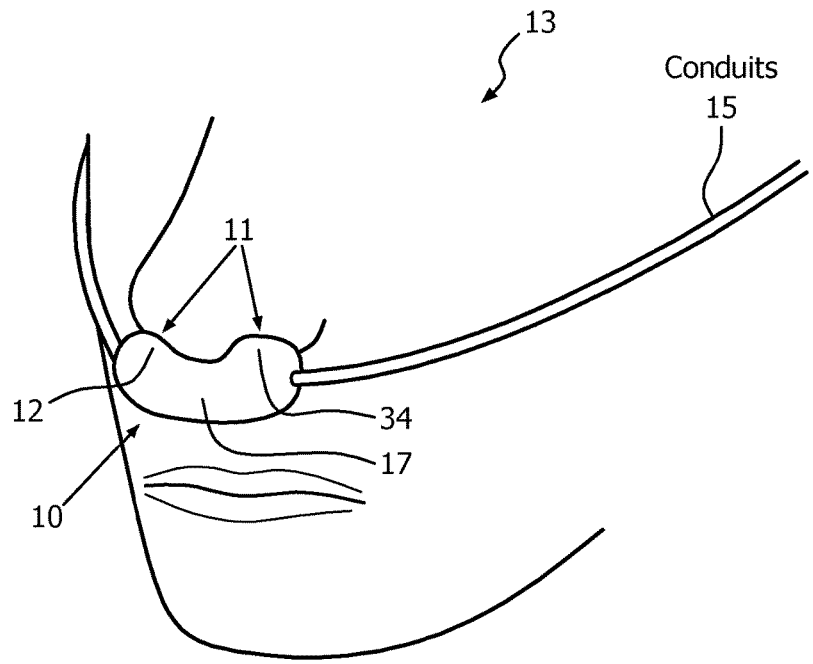
FIG. 2 illustrates the nasal apparatus engaging the nostrils of a subject.

By way of a non-limiting example, FIG. 2 illustrates apparatus 10 engaging the nostrils 11 of a subject 13. Apparatus 10 may be configured to couple with conduits 15 such that gas is conducted to and/or from the airway of subject 13 while apparatus 10 is engaged with nostrils 11 of subject 13. Conduits 15 may couple with apparatus 10 via interface fit, and/or other coupling mechanisms. In some embodiments, conduits 15 may terminate in luer locks and/or other coupling mechanisms, on the ends of conduits 15 located away from apparatus 10. Conduits 15 may be a flexible length of hose, or other conduit, that places apparatus 10 in fluid communication with one or more external devices (not shown in FIG. 2). The external devices may include devices related to respiratory therapy, respiratory monitoring, pressurized gas delivery, and/or other devices. The external devices may include devices related to positive airway pressure therapy. For example, the external devices may include a pressure generator configured to generate a pressurized flow of breathable gas for delivery to the airway of subject 13. The external devices may include one or more sensors configured to generate output signals conveying information related to gas parameters of the gas in apparatus 10, conduits 15, nostrils 11, and/or the external devices, for example. The present disclosure is not limited to these examples, and contemplates delivery of the flow of gas to the subject using other external devices.

Returning to FIG. 1, nasal apparatus 10 is configured without prongs, improving patient comfort. Apparatus 10 introduces no noticeable changes in patient work-of-breathing. The open system (e.g., a first ambient environment port 24) makes it possible to recreate the pressure-sensing environment externally, rather than deep within the nasal cavity, as is seen in existing designs. This eliminates the use of invasive pitot tubes in the form of prongs. The first ambient environment port 24 permits the acquisition and disposal of breathable gas to and from the patient's nasal passage, through a first breathing conduit 20. In the absence of a first ambient environment port, a patient's inspiratory and expiratory effort (work of breathing) may be affected, compromising the rate and volume of breathable gas transmitted to and from the patient. Apparatus 10 may be fabricated from lower (relative to conventional nasal cannulas) durometer elastomeric materials. At a constant wall thickness, lower durometer materials deform more easily under equal loading forces, exhibiting "cushion-like" properties. The "cushion-like" properties may allow apparatus 10 to be configured without conventional prongs but still be worn within the nasal passages, reducing or eliminating irritation and/or discomfort relative to conventional nasal cannula prongs. The "cushion-like" properties may enhance engagement between apparatus 10 and one or both nostrils.

Figure 3:
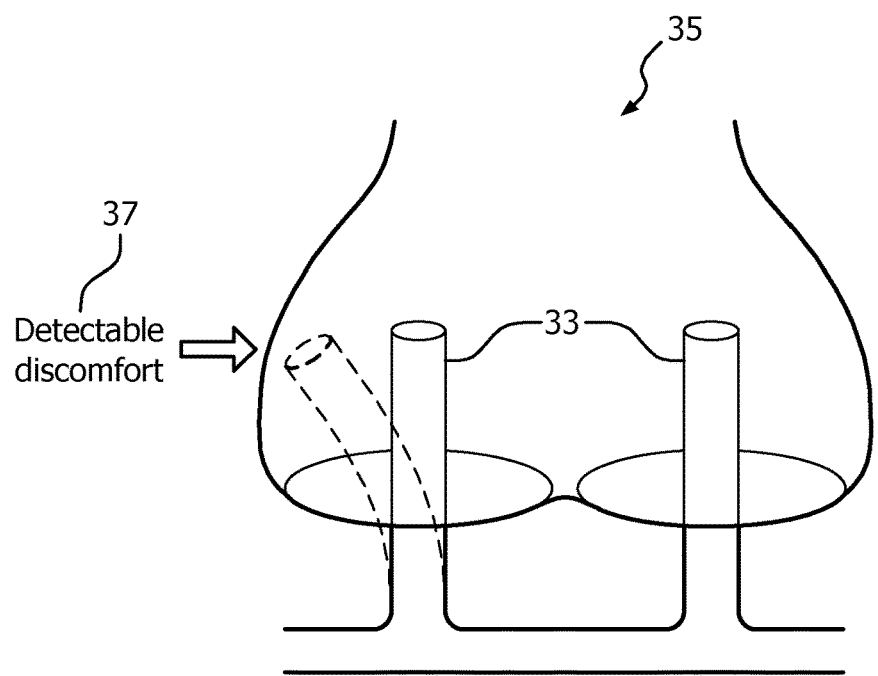
FIG. 3 illustrates discomfort caused by conventional nasal cannula prongs in a subject's nasal passages.
Figure 4:
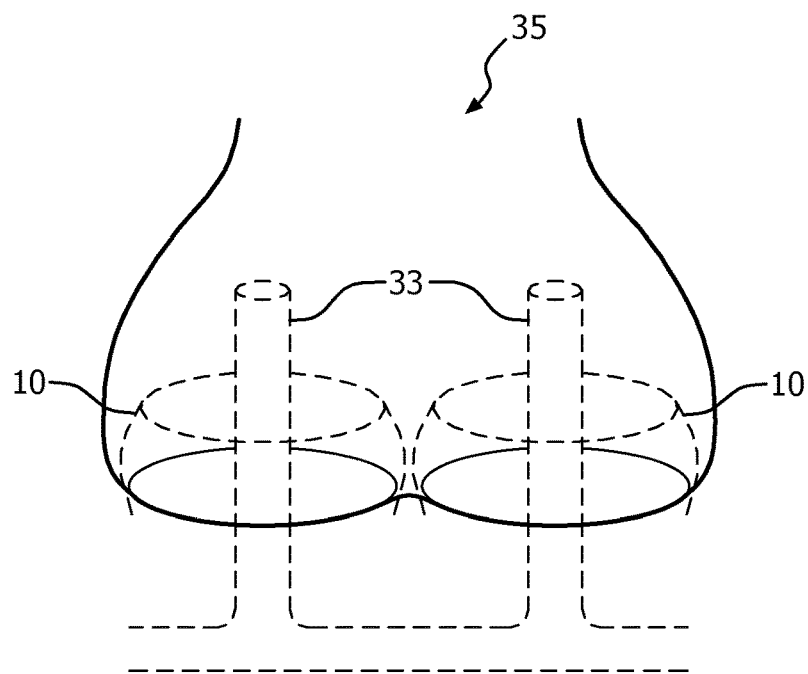
FIG. 4 illustrates differences between conventional nasal cannula prongs and the minimally invasive nasal apparatus in the nasal passages of a subject.

By way of a non-limiting example, FIG. 3 illustrates discomfort caused by conventional nasal cannula prongs 33 in a subject's nasal passages 35. FIG. 3 illustrates how prongs 33 may move 37 within nasal passages 35 and cause discomfort. FIG. 4 illustrates differences between conventional nasal cannula prongs 33 and apparatus 10 in nasal passages 35. FIG. 4 illustrates how apparatus 10 is configured without conventional prongs but still worn within nasal passages 35, reducing or eliminating irritation and/or discomfort relative to conventional nasal cannula prongs 33.

FIG. 5 illustrates a cross-sectional view of apparatus 10. FIG. 5 illustrates cross section A-A shown in FIG. 1. As shown in FIG. 5, various structures are formed in body 17. First nasal cannula system 12 comprises the first breathing conduit 20, a first nasal port 22, the first ambient environment port 24, a first pressure conduit 26, a first pressure port 28, a first sealing surface 30, a first flow deflection surface 32, and/or other components. Second nasal cannula system 34 comprises a second breathing conduit 40, a second nasal port 44, a second ambient environment port 46, a second pressure conduit 48, a second pressure port 50, a second sealing surface 52, a second flow deflection surface 54, and/or other components. The illustration of apparatus 10 shown in FIG. 5 is not intended to be limiting. In FIG. 5, apparatus 10 is shown including first nasal cannula system 12 and second nasal cannula system 34. In some embodiments, apparatus 10 made include only one of first nasal cannula system 12 or nasal cannula system 34. In some embodiments, apparatus 10 may comprise a single nasal cannula system configured to engage either nostril of a subject's nose.

First breathing conduit 20 is configured to conduct a pressurized flow of breathable gas into the first nasal passage of the subject through first nasal port 22 during inhalation, and conduct exhaled gas out of the first nasal passage to the ambient environment through the first ambient environment port 24 during exhalation. First nasal port 22 is open to the first nasal passage in the first nostril of the subject. First ambient environment port 24 is open to the ambient environment. Second breathing conduit 40 is configured to conduct the pressurized flow of breathable gas into the second nasal passage of the subject through second nasal port 44 during inhalation, and conduct exhaled gas out of the second nasal passage to the ambient environment through second ambient environment port 46 during exhalation. Second nasal port 44 is open to the second nasal passage in the second nostril of the subject. Second ambient environment port 46 is open to the ambient environment.

First breathing conduit 20 is formed in body 17 and extends from first nasal port 22 at a first end 100 of apparatus 10 to first ambient environment port 24 at a second end 102 of apparatus 10. First breathing conduit 20 may have a width 21 of less than about 0.50 inches. Width 21 may be between about 0.25 inches and about 0.50 inches. Width 21 may be about 0.33 inches. First nasal port 22 may have a substantially circular cross-sectional shape with a radius 23 of less than about 0.40 inches. Radius 23 may be between about 0.10 inches and about 0.40 inches. Radius 23 may be about 0.18 inches. In some embodiments, first nasal port 22 may have a cross-sectional shape other than circular. A portion of first breathing conduit 20 may form a chamber 60 adjacent to first nasal port 22 toward first end 100. Chamber 60 may have a surface 61 toward second end 102 that is shaped like an annular ring. First breathing conduit 20 and second breathing conduit 40 may be substantially parallel to each other along a first axis 101 of apparatus 10. From bridge 38, first breathing conduit 20 may be located toward a fourth end 106 of apparatus 10 and second breathing conduit 40 may be located toward a third end 104 of apparatus 10. Second breathing conduit 40 is formed in body 17 and extends from second nasal port 44 at first end 100 to second ambient environment port 46 at second end 102. Second breathing conduit 40 may have a width 41 of less than about 0.50 inches. Width 41 may be between about 0.25 inches and about 0.50 inches. Width 41 may be about 0.33 inches. Second nasal port 44 may have a substantially circular cross-sectional shape with a radius 45 of less than about 0.40 inches. Radius 45 may be between about 0.10 inches and about 0.40 inches. Radius 45 may be about 0.18 inches. In some embodiments, second nasal port 45 may have a cross-sectional shape other than circular. A portion of second breathing conduit 40 forms a chamber 62 adjacent to second nasal port 44 toward first end 100. Chamber 62 may have a surface 63 toward second end 102 that is shaped like an annular ring.

First pressure conduit 26 is configured to conduct the pressurized flow of breathable gas from first pressure port 28 to first breathing conduit 20 during inhalation. First pressure port 28 is configured to receive at least a portion of the pressurized flow of breathable gas during inhalation. Second pressure conduit 48 is configured to conduct the pressurized flow of breathable gas from second pressure port 50 to second breathing conduit 40 during inhalation. Second pressure port 50 is configured to receive at least a portion of the pressurized flow of breathable gas during inhalation.

First pressure port 28 is formed in body 17 at fourth end 106 of apparatus 10. First pressure conduit 26 extends from first pressure port 28 toward second end 102 and experiences a bend such that first pressure conduit 26 continues extending along a second axis 103 toward first breathing conduit 20. First pressure conduit 26 terminates at an orifice 64 in first breathing conduit 20. Second pressure port 50 is formed in body 17 at third end 104 of apparatus 10. Second pressure conduit 48 extends from second pressure port 50 toward second end 102 and experiences a bend such that second pressure conduit 48 continues extending along second axis 103 toward second breathing conduit 40. Second pressure conduit 48 terminates at an orifice 66 in second breathing conduit 40. In some embodiments, first pressure conduit 26 and/or second pressure conduit 48 may be generally cylindrically shaped, for example. In some embodiments, some or all of conduits 26 and/or 48 may have a cross section other than circular.

First sealing surface 30 surrounds first nasal port 22 and is configured to removably seal first nasal cannula system 12 with the first nostril to prevent gas from escaping between first sealing surface 30 and the first nostril. First sealing surface 30 forms a domed wall 31 of chamber 60 toward first end 100. Domed wall 31 may have a radius 39 of less than about 0.4 inches. Radius 39 may be between about 0.2 inches and about 0.4 inches. Radius 39 may be about 0.3 inches. First nasal port 22 is located at a peak of the dome at first end 100. Second sealing surface 52 surrounds second nasal port 44 and is configured to removably seal second nasal cannula system 34 with the second nostril to prevent gas from escaping between second sealing surface 52 and the second nostril. Second sealing surface 52 forms a domed wall 53 of chamber 62 toward first end 100. Domed wall 53 may have a radius 55 of less than about 0.4 inches. Radius 55 may be between about 0.2 inches and about 0.4 inches. Radius 55 may be about 0.3 inches. Second nasal port 44 is located at a peak of the dome at first end 100. Sealing surfaces 30 and/or 52 may be formed from relatively low durometer elastomeric materials. Sealing surfaces 30 and/or 52 may be configured to flex and/or deform when apparatus 10 engages the nostrils of the subject such that a removable seal is formed with each nostril. The flexibility and/or deformability of sealing surfaces 30 and or 52 may be changed by varying a wall thickness of the domed walls 31 and/or 53, varying arched dimensions of the dome created by sealing surfaces 30, varying the size of ports 22 and/or 44, and/or 52, and/or varying other factors.

Figure 5A:
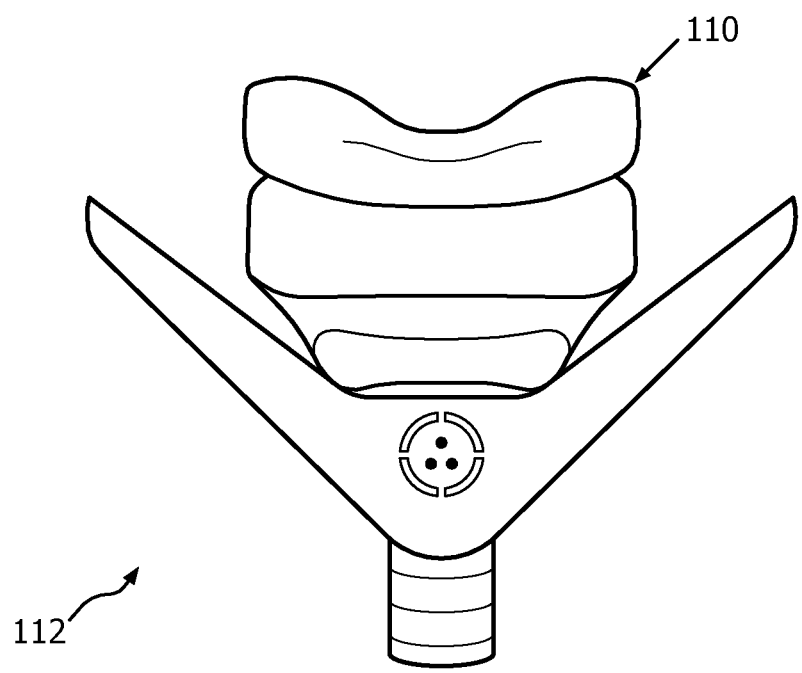
FIG. 5A illustrates a cradle style cushion configured to removably seal an apparatus with both nostrils.

In some embodiments, first sealing surface 30 may be configured to surround first nasal port 22 and removably seal first nasal cannula system 12 with one or both nostrils to prevent gas from escaping between first sealing surface 30 and one or both nostrils. For example, FIG. 5A illustrates a cradle style cushion 110 configured to removably seal an apparatus 112 with both nostrils (nostrils not shown in FIG. 5A). In some embodiments, cradle style cushion 110, sealing surface 30 (shown in FIG. 5), and/or other sealing surfaces may couple with a nasal apparatus comprising a single nasal cannula system.

Returning to FIG. 5, first flow deflection surface 32 is configured to deflect at least a portion of the exhaled gas from first breathing conduit 20 into first pressure conduit 26 during exhalation. First flow deflection surface 32 is configured to deflect the portion of exhaled gas such that one or more gas parameters of the gas in first pressure conduit 26 are impacted sufficiently to facilitate quantification of such one or more gas parameters in the first nasal passage of the subject from measurements taken on the pressurized flow of breathable gas upstream from delivery from first breathing conduit 20 into the first nasal passage of the subject. Second flow deflection surface 54 is configured to deflect at least a portion of the exhaled gas from second breathing conduit 40 into second pressure conduit 48 during exhalation such that one or more gas parameters in the second pressure conduit are impacted sufficiently to facilitate quantification of such one or more gas parameters in the second nasal passage of the subject from measurements taken on the pressurized flow of breathable gas upstream from delivery from second breathing conduit 40 into the second nasal passage of the subject.

Upstream measurement locations may include locations within and/or in communication with apparatus 10, within and/or in communication with conduits 15 (shown in FIG. 2), and/or within and/or in communication with other external devices (discussed herein). In some embodiments, the upstream measurements may include separate measurements for gas parameters in one nostril or the other nostril separately. In some embodiments, the measurements may include combined measurements of gas parameters is both nostrils collectively. The one or more gas parameters may include, for example, one or more of flow rate, pressure, humidity, gas composition, temperature, volume, and/or other parameters.

First flow deflection surface 32 is formed in a sidewall 70 of first breathing conduit 20 where sidewall 70 meets surface 61 toward fourth end 106. First flow deflection surface 32 may be located at and/or near orifice 64 where first pressure conduit 26 joins first breathing conduit 20. Second flow deflection surface 54 is formed in a sidewall 72 of second breathing conduit 40 where sidewall 72 meets surface 63 toward third end 104. Second flow deflection surface 54 may be located at and/or near orifice 66 where second pressure conduit 48 joins second breathing conduit 40.

Flow deflection surfaces 32 and/or 54 may have arcuate form factors with radii of less than about 0.15 inches. The radii may be between about 0.05 inches and about 0.15 inches. The radii may be about 0.09 inches. The arcuate flow deflection surfaces 32 and/or 54 may open toward first end 100 and be formed in side walls 70 and/or 72 such that a depth 90, 92 of flow deflection surfaces 32 and/or 54 extends toward second end 102 past pressure conduits 26 and/or 48. Flow deflection surfaces 32 and/or 54 may have lengths 94, 96 of less than about 0.25 inches. Lengths 94, 96 may be between about 0.10 inches and about 0.25 inches. Lengths 94, 96 may be about 0.17 inches. The form factor and/or dimensions of flow deflection surfaces 32 and/or 54 shown in FIG. 5 and described herein are not intended to be limiting. The form factor and/or dimensions of flow deflection surfaces 32 and/or 54 may be adjusted to change the amount of gas deflected into pressure conduits 26 and/or 48, and/or may be adjusted for other reasons.

Figure 6:
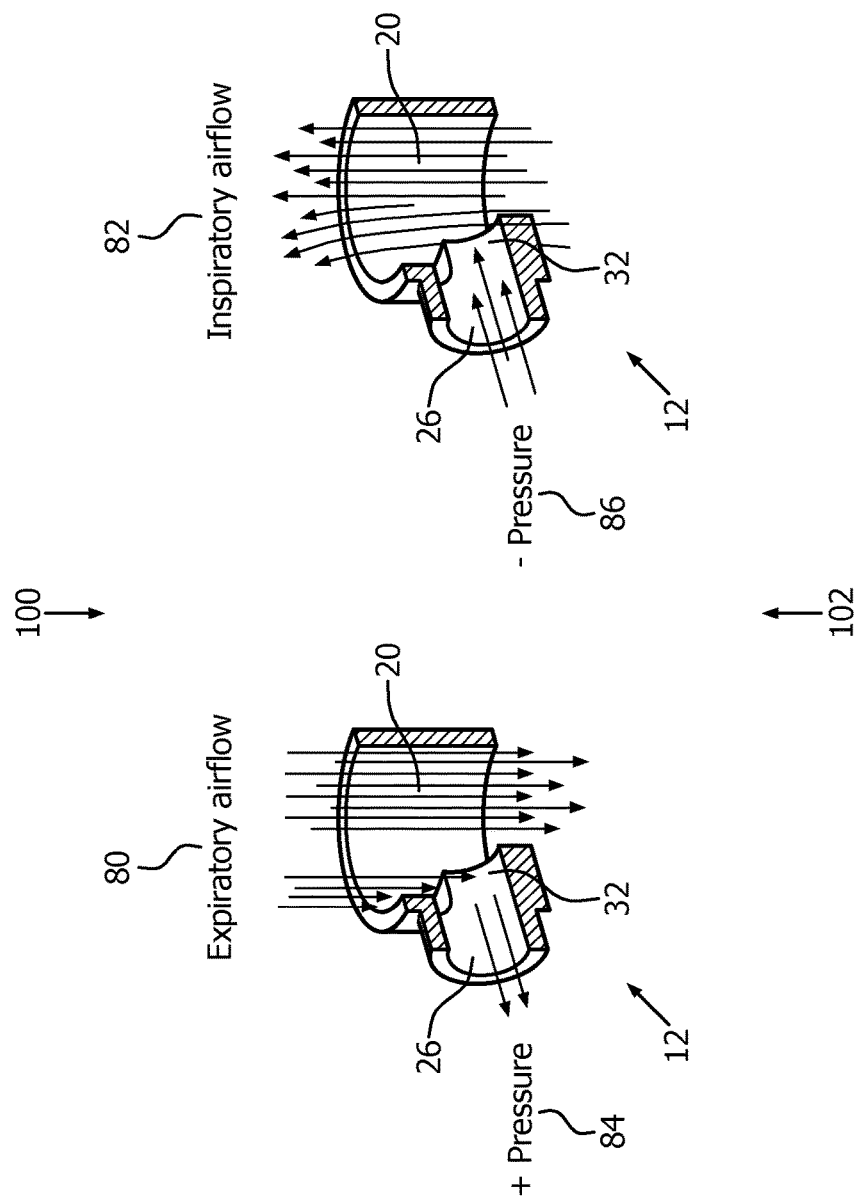
FIG. 6 illustrates expiratory airflow and inspiratory airflow through a portion of a nasal cannula system.

By way of a non-limiting example, FIG. 6 illustrates expiratory airflow 80 and inspiratory airflow 82 through a portion of first nasal cannula system 12. During expiratory airflow 80, breathable gas flows through first breathing conduit 20 from first end 100 (engagement with the nostril not shown) toward second end 102 (first ambient environment port 24 not shown). At least a portion of the breathable gas is deflected by first flow deflection surface 32 into first pressure conduit 26, creating a positive pressurized flow 84 in first pressure conduit 26. During inspiratory airflow 82, breathable gas flows through first breathing conduit 20 from second end 102 toward first end 100, drawing breathable gas through first pressure conduit 26 and creating a negative pressurized flow 86 in first pressure conduit 26. In some embodiments, a pressurized flow of breathable gas may be delivered to the subject during inhalation through first pressure conduit 26.

Returning to FIG. 5, apparatus 10 is configured such that responsive to first sealing surface 30 and/or second sealing surface 52 removably sealing first nasal cannula system 12 with the first nostril and/or second nasal cannula system 34 with the second nostril, first flow deflection surface 32, second flow deflection surface 54, first pressure conduit 26, second pressure conduit 48, first ambient environment port 24, and second ambient environment port 46 are located externally to the first and/or the second nasal passage.

Figure 7:
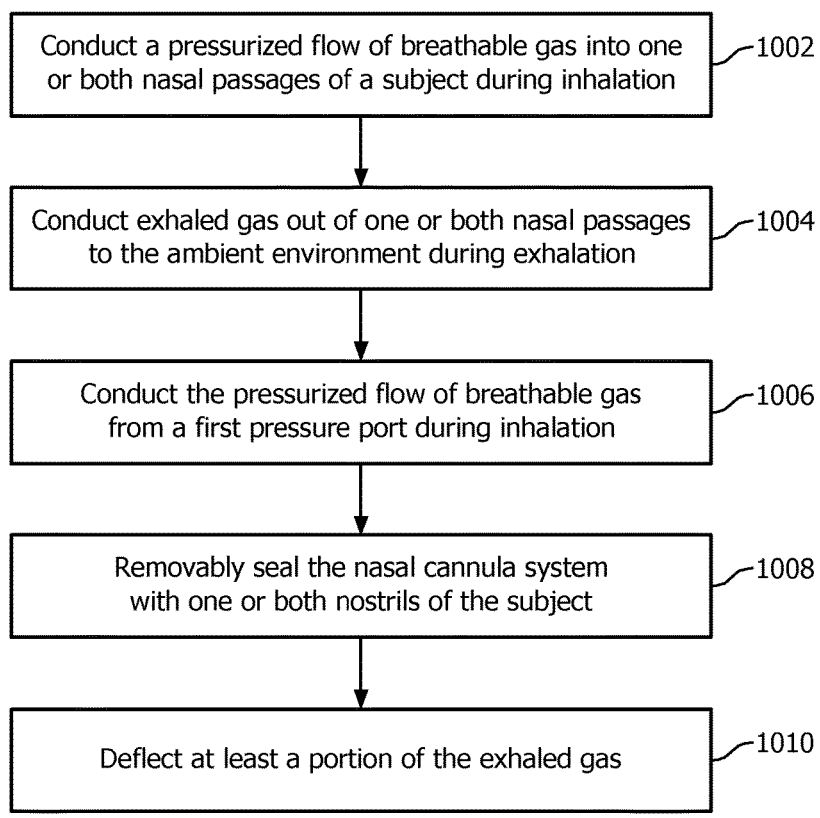
FIG. 7 illustrates a method for engaging a nose of a subject with the minimally invasive nasal apparatus.

FIG. 7 illustrates a method 1000 for engaging a nose of a subject with a minimally invasive nasal apparatus. The apparatus comprises a first nasal cannula system. The first nasal cannula system comprises a first breathing conduit, a first pressure conduit, a first sealing surface, and a first flow deflection surface. The nose of the subject includes a first nostril, a second nostril, a first nasal passage, and a second nasal passage. The operations of method 1000 presented below are intended to be illustrative. In some embodiments, method 1000 may be accomplished with one or more additional operations not described, and/or without one or more of the operations discussed. Additionally, the order in which the operations of method 1000 are illustrated in FIG. 7 and described below is not intended to be limiting.

In some embodiments, method 1000 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 1000 in response to instructions stored electronically on an electronic storage medium. The one or more processing devices may include one or more devices configured through hardware, firmware, and/or software to be specifically designed for execution of one or more of the operations of method 1000.

At an operation 1002, a pressurized flow of breathable gas is conducted, with the first breathing conduit, into one or both nasal passages of the subject through a first nasal port during inhalation. The first nasal port is open to one or both nasal passages of the subject. In some embodiments, operation 1002 is performed by a first breathing conduit the same as or similar to first breathing conduit 20 (shown in FIG. 5 and described herein).

At an operation 1004, exhaled gas is conducted out of one or both nasal passages to the ambient environment through a first ambient environment port during exhalation. The first ambient environment port is open to the ambient environment. In some embodiments, operation 1004 is performed by a first breathing conduit the same as or similar to first breathing conduit 20 (shown in FIG. 5 and described herein).

At an operation 1006, the pressurized flow of breathable gas is conducted, with the first pressure conduit, from a first pressure port to the first breathing conduit during inhalation. The first pressure port is configured to receive the pressurized flow of breathable gas during inhalation. In some embodiments, operation 1006 is performed by a first pressure conduit the same as or similar to first pressure conduit 26 (shown in FIG. 5 and described herein).

At an operation 1008, the first nasal port is surrounded, with the first sealing surface, and the first sealing surface removably seals the first nasal cannula system with one or both nostrils to prevent gas from escaping between the first sealing surface and one or both nostrils. In some embodiments, operation 1008 is performed by a first sealing surface the same as or similar to first sealing surface 30 (shown in FIG. 5 and described herein).

At an operation 1010, at least a portion of the exhaled gas is deflected, with the first flow deflection surface, from the first breathing conduit into the first pressure conduit during exhalation. The portion of gas is deflected such that one or more gas parameters of the gas in the first pressure conduit are impacted sufficiently to facilitate quantification of such one or more gas parameters in one or both nasal passages of the subject from measurements taken on the pressurized flow of breathable gas upstream from delivery from the first breathing conduit into one or both nasal passages of the subject. In some embodiments, operation 1010 is performed by a first flow deflection surface the same as or similar to first flow deflection surface 32 (shown in FIG. 5 and described herein).

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the description provided above provides detail for the purpose of illustration based on what is currently considered to be the most practical and preferred embodiments, it is to be understood that such detail is solely for that purpose and that the disclosure is not limited to the expressly disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

What is claimed is:

1. A nasal apparatus comprising a first nasal cannula system configured to engage a nose of a subject, the nose including a first nostril, a second nostril, a first nasal passage, and a second nasal passage; the first nasal cannula system comprising:

a first breathing conduit configured to conduct a pressurized flow of breathable gas into one or both nasal passages of the subject through a first nasal port during inhalation, and conduct exhaled gas out of one or both nasal passages to the ambient environment through a first ambient environment port during exhalation, the first nasal port open to one or both nasal passages of the subject, the first ambient environment port open to the ambient environment;

a first pressure conduit configured to conduct the pressurized flow of breathable gas from a first pressure port to the first breathing conduit during inhalation, the first pressure port configured to receive the pressurized flow of breathable gas during inhalation;

a first sealing surface surrounding the first nasal port configured to removably seal the first nasal cannula system with one or both nostrils to prevent the pressurized flow of breathable gas from escaping between the first sealing surface and one or both nostrils; and a first flow deflection surface configured to deflect at least a portion of the exhaled gas from the first breathing conduit into the first pressure conduit during exhalation to facilitate quantification of one or more gas parameters of the pressurized flow of breathable gas in one or both nasal passages of the subject from measurements taken on the pressurized flow of breathable gas upstream of delivery from the first breathing conduit into one or both nasal passages of the subject.

2. The apparatus of claim 1, wherein the first sealing surface is made of a low durometer elastomeric material.

3. The apparatus of claim 1, wherein the first nasal cannula system is configured such that responsive to the first sealing surface removably sealing the first nasal cannula system with one or both nostrils, the first flow deflection surface, the first pressure conduit, and the first ambient environment port are external to one or both nasal passages.

4. The apparatus of claim 1, further comprising a second nasal cannula system, wherein the first nasal cannula system is configured to engage the first nostril of the subject and the second nasal cannula system is configured to engage the second nostril of the subject, the second nasal cannula system joined to the first nasal cannula system by a bridge such that the first nasal cannula system engages the first nostril and the second nasal cannula system engages the second nostril at the same time.

5. The apparatus of claim 4, wherein the second nasal cannula system comprises:
   a second breathing conduit configured to conduct the pressurized flow of breathable gas into the second nasal passage of the subject through a second nasal port during inhalation, and conduct exhaled gas out of the second nasal passage to the ambient environment through a second ambient environment port during exhalation, the second nasal port open to the second nasal passage in the second nostril of the subject, the second ambient environment port open to the ambient environment;
   a second pressure conduit configured to conduct the pressurized flow of breathable gas from a second pressure port to the second breathing conduit during inhalation, the second pressure port configured to receive the pressurized flow of breathable gas during inhalation;
   a second sealing surface surrounding the second nasal port configured to removably seal the second nasal cannula system with the second nostril to prevent the pressurized flow of breathable gas from escaping between the second sealing surface and the second nostril; and
   a second flow deflection surface configured to deflect at least a portion of the exhaled gas from the second breathing conduit into the second pressure conduit during exhalation to facilitate quantification of one or more gas parameters of the pressurized flow of breathable gas in the second nasal passage of the subject from measurements taken on the pressurized flow of breathable gas upstream of delivery from the second breathing conduit into the second nasal passage of the subject.

6. The apparatus of claim 1, wherein the first flow deflection surface is located at an orifice where the first pressure conduit joins the first breathing conduit.

7. The apparatus of claim 1, wherein the first sealing surface forms a dome shaped chamber.

8. The apparatus of claim 7, wherein the first nasal port is located at a peak of the chamber.

9. The apparatus of claim 8, wherein the chamber comprises a surface shaped in an annular ring within the chamber.

10. The apparatus of claim 9, wherein the first flow deflection surface is formed in a sidewall of the first breathing conduit, wherein the sidewall meets the surface of the chamber.

11. A method for engaging a nose of a subject with a nasal apparatus, the apparatus comprising a first nasal cannula system, the first nasal cannula system comprising a first breathing conduit, a first pressure conduit, a first sealing surface, and a first flow deflection surface, the nose including a first nostril, a second nostril, a first nasal passage, and a second nasal passage; the method comprising:

conducting, with the first breathing conduit, a pressurized flow of breathable gas into one or both nasal passages of the subject through a first nasal port during inhalation, and conducting exhaled gas out of one or both nasal passages to the ambient environment through a first ambient environment port during exhalation, the first nasal port open to one or both nasal passages of the subject, the first ambient environment port open to the ambient environment;
conducting, with the first pressure conduit, the pressurized flow of breathable gas from a first pressure port to the first breathing conduit during inhalation, the first pressure port configured to receive the pressurized flow of breathable gas during inhalation;
surrounding, with the first sealing surface, the first nasal port, and removably sealing, with the first sealing surface, the first nasal cannula system with one or both nostrils to prevent the pressurized flow of breathable gas from escaping between the first sealing surface and one or both nostrils; and
deflecting, with the first flow deflection surface, at least a portion of the exhaled gas from the first breathing conduit into the first pressure conduit during exhalation to facilitate quantification of one or more gas parameters of the pressurized flow of breathable gas in one or both nasal passages of the subject from measurements taken on the pressurized flow of breathable gas upstream of delivery from the first breathing conduit into one or both nasal passages of the subject.

12. The method of claim 11, wherein the first sealing surface is made of a low durometer elastomeric material.

13. The method of claim 11, wherein conducting the exhaled gas out of one or both nasal passages to the ambient environment through the first ambient environment port during exhalation, conducting the pressurized flow of breathable gas from the first pressure port to the first breathing conduit during inhalation, and deflecting the portion of the exhaled gas from the first breathing conduit into the first pressure conduit during exhalation occur external to one or both nasal passages.

14. The method of claim 11, further comprising engaging the first nostril with the first nasal cannula system and engaging the second nostril of the subject with a second nasal cannula system, the second nasal cannula system joined to the first nasal cannula system by a bridge such that the first nasal cannula system engages the first nostril and the second nasal cannula system engages the second nostril at the same time.

15. The method of claim 14, further comprising:
conducting, with a second breathing conduit, the pressurized flow of breathable gas into the second nasal passage of the subject through a second nasal port during inhalation, and conducting exhaled gas out of the second nasal passage to the ambient environment through a second ambient environment port during exhalation, the second nasal port open to the second nasal passage in the second nostril of the subject, the second ambient environment port open to the ambient environment;
conducting, with a second pressure conduit, the pressurized flow of breathable gas from a second pressure port to the second breathing conduit during inhalation, the second pressure port configured to receive the pressurized flow of breathable gas during inhalation;
surrounding, with a second sealing surface, the second nasal port and removably sealing, with the second sealing surface, the second nasal cannula system with the second nostril to prevent the pressurized flow of breathable gas from escaping between the second sealing surface and the second nostril; and deflecting, with a second flow deflection surface, at least a portion of the exhaled gas from the second breathing conduit into the second pressure conduit during exhalation to facilitate quantification of such one or more gas parameters of the pressurized flow of breathable gas in the second nasal passage of the subject from measurements taken on the pressurized flow of breathable gas upstream of delivery from the second breathing conduit into the second nasal passage of the subject.

16. A nasal apparatus comprising a means for engaging a nose of a subject, the nose including a first nostril, a second nostril, a first nasal passage, and a second nasal passage; the means for engaging comprising:

means for conducting a pressurized flow of breathable gas into one or both nasal passages of the subject through a first nasal port during inhalation, and conducting exhaled gas out of one or both nasal passages to the ambient environment through a first ambient environment port during exhalation, the first nasal port open to one or both nasal passages of the subject, the first ambient environment port open to the ambient environment;

means for conducting the pressurized flow of breathable gas from a first pressure port to the means for conducting the pressurized flow of breathable gas into one or both nasal passages through the first nasal port during inhalation, the first pressure port configured to receive the pressurized flow of breathable gas during inhalation;

means for surrounding the first nasal port and removably sealing the means for engaging the nose of the subject with one or both nostrils to prevent gas from escaping between the means for surrounding and sealing and one or both nostrils; and means for deflecting at least a portion of the exhaled gas from the means for conducting the pressurized flow of breathable gas into one or both nasal passages of the subject into the means for conducting the pressurized flow of breathable gas from the first pressure port during exhalation to facilitate quantification of one or more gas parameters of the pressurized flow of breathable gas in one or both nasal passages of the subject from c measurements taken on the pressurized flow of breathable gas upstream of delivery from the means for conducting the pressurized flow of breathable gas into one or both nasal passages of the subject.

17. The apparatus of claim 16, wherein the means for surrounding and sealing is made of a low durometer elastomeric material.

18. The apparatus of claim 16, wherein the means for engaging the nose of the subject is configured such that responsive to the means for surrounding and sealing removably sealing the means for engaging with one or both nostrils, the means for deflection, the means for conducting the pressurized flow of breathable gas from the first pressure port, and the first ambient environment port are external to one or both nasal passages.

19. The apparatus of claim 16, further comprising means for engaging the second nostril of the subject, wherein the means for engaging one or both nostrils is configured to engage the first nostril of the subject, the means for engaging the second nostril joined to the means for engaging one or both nostrils by means for bridging such that the means for engaging one or both nostrils engages the first nostril and the means for engaging the second nostril engages the second nostril at the same time.

20. The apparatus of claim 19, wherein the means for engaging the nose of the subject further comprises:

means for conducting the pressurized flow of breathable gas into the second nasal passage of the subject through a second nasal port during inhalation, and conducting exhaled gas out of the second nasal passage to the ambient environment through a second ambient environment port during exhalation, the second nasal port open to the second nasal passage in the second nostril of the subject, the second ambient environment port open to the ambient environment;

means for conducting the pressurized flow of breathable gas from a second pressure port to the means for conducting the pressurized flow of breathable gas into the second nasal passage through the second nasal port during inhalation, the second pressure port configured to receive the pressurized flow of breathable gas during inhalation;

means for surrounding the second nasal port and removably sealing the means for engaging the nose of the subject with the second nostril to prevent gas from escaping between the means for surrounding and sealing and the second nostril; and means for deflecting at least a portion of the exhaled gas from the means for conducting the pressurized flow of breathable gas into the second nasal passage of the subject into the means for conducting the pressurized flow of breathable gas from the second pressure port during exhalation to facilitate quantification of one or more gas parameters of the pressurized flow of breathable gas in the second nasal passage of the subject from measurements taken on the pressurized flow of breathable gas upstream of delivery from the means for conducting the pressurized flow of breathable gas into the second nasal passage of the subject.

* * * * *